United States Patent [19]
Dunn et al.

[11] 4,079,738
[45] Mar. 21, 1978

[54] NEEDLE RESTRAINING APPARATUS

[75] Inventors: Karl L. Dunn, Salt Lake City; Gordon S. Reynolds, Bountiful; Karl A. Pannier, Jr.; James L. Sorenson, both of Salt Lake City, all of Utah

[73] Assignee: Sorenson Research Co., Inc., Salt Lake City, Utah

[21] Appl. No.: 724,486

[22] Filed: Sep. 20, 1976

[51] Int. Cl.$^2$ ...................... A61M 5/00; A61M 25/00
[52] U.S. Cl. .......................... 128/214.4; 128/DIG. 16
[58] Field of Search ............ 128/214.4, 221, DIG. 16, 128/348

[56] References Cited

U.S. PATENT DOCUMENTS

| | | | |
|---|---|---|---|
| 2,389,355 | 11/1945 | Goland et al. | 128/214.4 |
| 3,459,183 | 8/1969 | Ring et al. | 128/214.4 |
| 3,537,451 | 11/1970 | Beck et al. | 128/214.4 |
| 3,727,613 | 4/1973 | Sorenson et al. | 128/214.4 |
| 3,769,975 | 11/1973 | Nimoy et al. | 128/214.4 |
| 3,875,938 | 4/1975 | Mellor | 128/214.4 |

FOREIGN PATENT DOCUMENTS

| | | | |
|---|---|---|---|
| 265,972 | 10/1913 | Germany | 128/214.4 |

*Primary Examiner*—Dalton L. Truluck
*Attorney, Agent, or Firm*—H. Ross Workman; J. Winslow Young

[57] ABSTRACT

Needle restraining apparatus is provided which serves to prevent a stylet needle of a venipuncture device which fits telescopically within a catheter of the venipuncture device from longitudinally moving with respect to the catheter during venipuncture. In one embodiment, the needle restraining apparatus provides a collar constructed of heat-shrinkable plastic releasably conforming to a needle hub and the hub of a tube adaptor of the venipuncture device. The collar is shrunk so that the leading and trailing ends of the collar form a non-slip fit over the irregular contour of the hub of the tube adaptor and the hub of the stylet needle. In a second embodiment of the invention, the collar is constructed of rigid plastic and preformed to engage the hub of the tube adaptor of the device and the hub of the stylet needle thereby preventing longitudinal movement of the stylet needle relative to the catheter. Structure is provided whereby the collar can be easily released to permit removal of the stylet needle from the venipuncture device after a venipuncture has been made.

20 Claims, 10 Drawing Figures

NEEDLE RESTRAINING APPARATUS

BACKGROUND

1. Field of the Invention

The present invention relates to venipuncture devices having a stylet needle which fits telescopically within a catheter and more particularly to needle restraining apparatus for preventing longitudinal movement of the stylet needle relative to the catheter during venipuncture.

2. The Prior Art

Venipuncture devices of a type having a rigid stylet needle which fits telescopically within a catheter are well known in the prior art. Typically, this type of venipuncture device is designed so that a beveled point of the stylet needle extends through the distal end of the catheter of the device. In this manner, the sharp beveled point of the stylet needle is used to break the patient's skin when making a venipuncture. Once the venipuncture has been made, the stylet needle can then be withdrawn through the catheter thereby leaving only the catheter within the patient's arm. Suitable tubes for purposes of intravenous feeding, collecting blood samples, transfusions or the like can then be connected to the hub of the tube adaptor of the catheter. Examples of this type of device are illustrated in U.S. Pat. No. 3,875,938.

In using the type of venipuncture device described above to make a venipuncture in a patient's arm, it frequently happens that the person using the device holds it at or near the hub of the tube adaptor of the device. This is the logical place to hold the device since it is closest to the beveled point of the stylet needle, thereby affording a more accurate and controlled insertion of the needle. However, when the venipuncture device is held as indicated by the tube adaptor, as the user attempts to make a venipuncture in the patient's skin, a rearwardly directed force is applied to the stylet needle causing it to slip through the catheter and tube adaptor until the beveled point of the stylet needle is obscured. This greatly increases the difficulty and pain associated with making a venipuncture since the catheter may become damaged and be undesirable for insertion through the patient's skin.

In order to prevent the stylet needle from sliding through the catheter of the device while making a venipuncture, it is necessary for the person using a conventional venipuncture device to hold it further back from the exposed beveled point of the needle at or near the hub of the needle. However, when holding the venipuncture device by the hub of the needle, it becomes very difficult to make an accurately controlled insertion into a vein in the patient's arm because the device is held at a point that is distant from the point of the needle.

Until this present invention, there has not been a venipuncture device available which combined the advantages of preventing the stylet needle of the device from being pushed back through the catheter of the device during venipuncture while at the same time allowing the user to hold the device by the tube adaptor near the distal end of the needle thereby maintaining the accuracy with which the point of the needle can be inserted into a vein in the patient's arm.

BRIEF SUMMARY AND OBJECTS OF THE INVENTION

The present invention comprises novel needle restraining apparatus for use with a venipuncture device having a stylet needle that fits telescopically within a catheter. The invention prevents longitudinal movement of the needle through the catheter during the venipuncture process. The needle restraining apparatus is also provided with structure that accommodates release of the apparatus once the venipuncture has been made.

It is therefore a primary object of the present invention to provide novel restraining apparatus and method for preventing longitudinal movement of a stylet needle of a venipuncture device relative to a catheter of the device during venipuncture.

Another object of the present invention is to provide structure accommodating release of the needle restraining apparatus after venipuncture so that the stylet needle may be withdrawn through the rear end of the catheter.

These and other objects and features of the present invention will become more fully apparent from the following description and appended claims taken in conjunction with the accompanying drawings.

DETAILED DESCRIPTION OF THE PREFERRED EMBODIMENTS

Attention is now turned to the detailed description of the invention as illustrated in the accompanying drawings wherein like parts have like numerals throughout.

As used throughout this specification, needle restraining apparatus shall mean a needle restraining collar and the structure of a venipuncture device adapted to coact with the collar to prevent longitudinal movement of a stylet needle relative to a catheter during the venipuncture process.

THE EMBODIMENTS OF FIGURES 1-3

Figure 1:
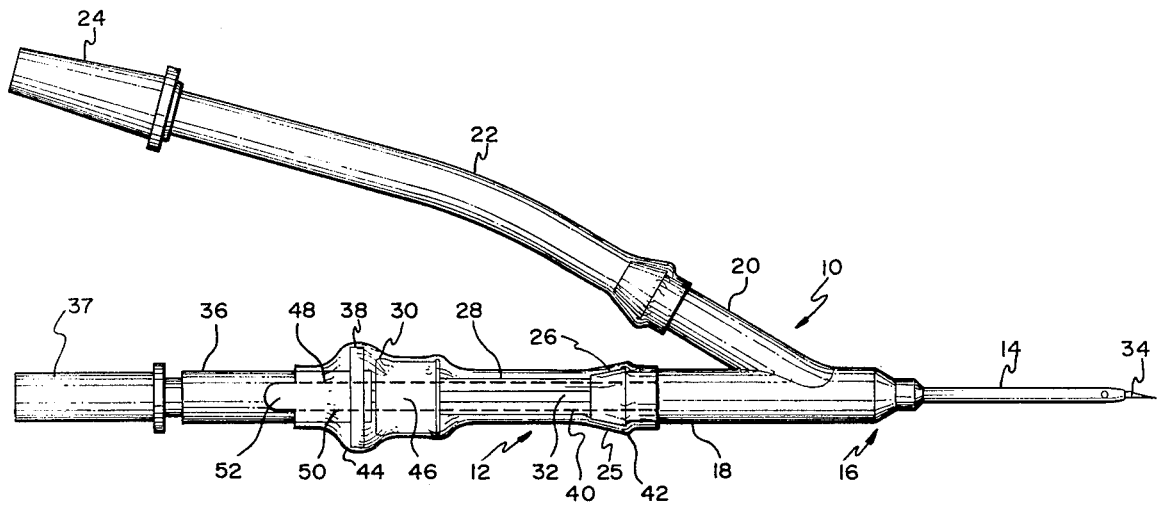
FIG. 1 is a side elevational view of a presently preferred embodiment of the needle restraining apparatus used in a conjunction with a venipuncture device having a Y-channel tube adaptor.

FIG. 1 illustrates one conventional type of venipuncture device generally designated 10 with which a needle restraining collar generally designated 12 may be used. The venipuncture device 10 has at its leading end a radiopaque teflon catheter 14. The catheter 14 is attached to a tube adaptor generally designated 16 which has a body portion 18 and a branch 20 joined to the body 18 in the form of a Y. The upwardly projecting branch 20 fits telescopically within a tube 22. The tube 22 is provided with a cap 24 which may be removed to permit the tube 22 to be connected to other tubes, e.g. blood tubing.

Figure 3:
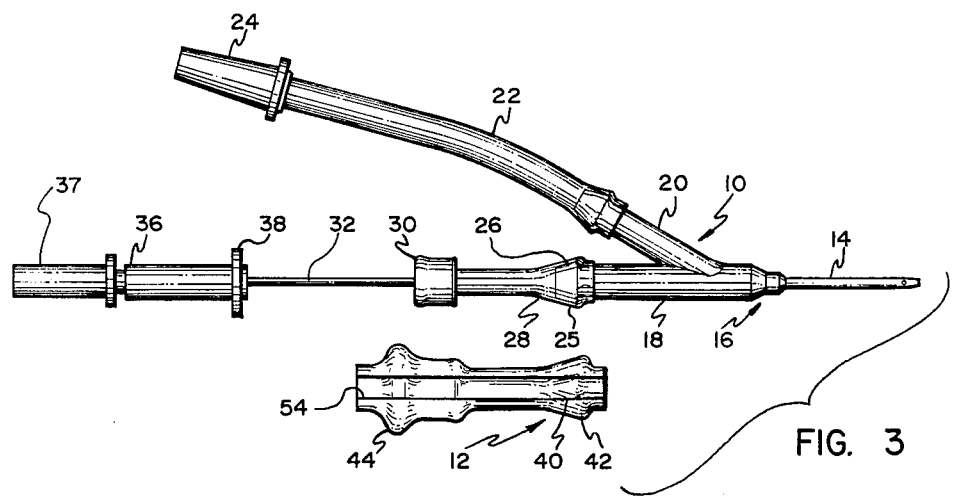
FIG. 3 is a side elevational view of the venipuncture device and needle restraining apparatus of FIG. 1 showing the stylet needle of the venipuncture device partly withdrawn from the catheter and tube adaptor of the device after removal of the collar.

As more clearly illustrated in FIG. 3, the body portion 18 of tube adaptor 16 has a hub 25 which fits telescopically within a silastic sleeve 28. The hub 25 of the tube adaptor 16 has a forwardly projecting frustoconically shaped flange 26 over which the forward end of the silastic sleeve 28 fits. The elastic properties of the silastic sleeve 28 allow the sleeve 28 to conform to the surface contour of the hub 25 formed by the forwardly projecting flange 26 thereby insuring a tight friction fit over the hub 25. Furthermore, flange 26 also helps to secure the needle restraining collar 12 to the hub 25 of the tube adaptor 16 as hereinafter more fully described.

At its trailing end, the sleeve 28 has a membrane 30 made of self-sealing material, such as rubber, through which the metal stylet needle 32 passes. The membrane 30 automatically seals the opening (not shown) through which the stylet needle 32 passes after the stylet needle 32 has been withdrawn from the adaptor 16 and sleeve 28 thereby preventing leakage of blood or other fluids without having to occlude the sleeve 28. The membrane 30 also permits the stylet needle 32 or any other type of hypodermic needle to be reinserted when injection of fluids is desired. Alternatively, membrane 30 may also be removed from the end of the sleeve 28 thereby permitting other tubes to be connected to sleeve 28.

Figure 2:
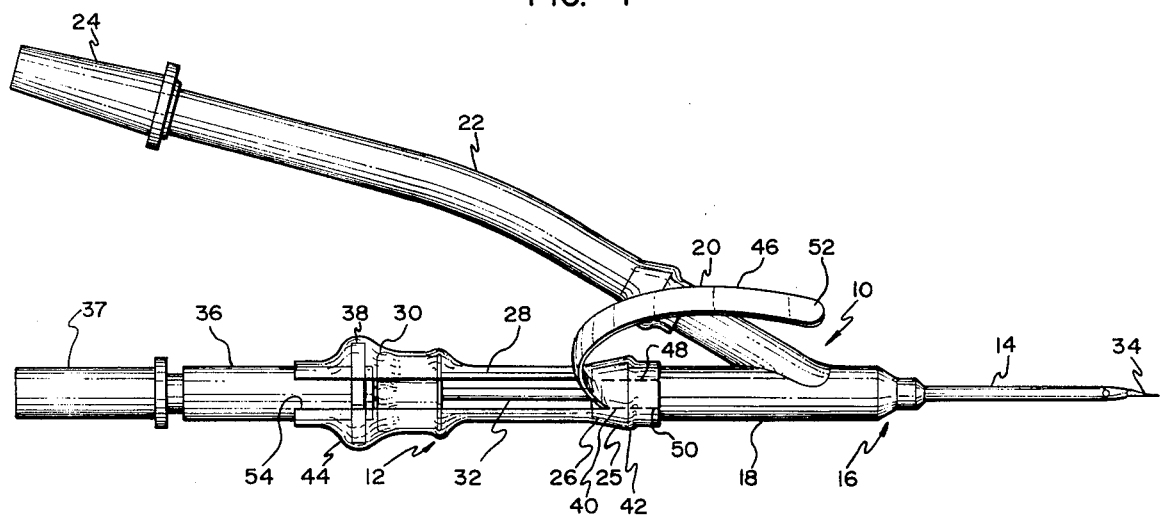
FIG. 2 is a side elevational view of the needle restraining apparatus shown in FIG. 1 illustrating the technique whereby the collar of the needle restraining apparatus is released.

As shown in FIGS. 1 and 2, the stylet needle 32 projects telescopically forward through the membrane 30, the silastic sleeve 28, the tube adaptor 16 and the teflon catheter 14 until the sharpened beveled point 34 of the stylet needle 32 extends slightly beyond the distal end of the teflon catheter 14. This allows the beveled point 34 of the stylet needle 32 to be used to puncture the patient's skin when making a venipuncture thereby facilitating insertion of the catheter 14.

As more clearly illustrated in FIG. 3, the stylet needle 32 is secured at its trailing end to a needle hub 36 having a radially projecting flange 38. As hereinafter more fully described, the radially projecting flange 38 helps to secure the needle restraining collar 12 to the needle hub 36.

The inside of the needle hub 36 forms a throughbore (not shown) which communicates with the lumen of stylet needle 32. The trailing end of the needle hub 36 is selectively sealed with a plug 37 which fits in mating relationship into the throughbore (not shown) of needle hub 36. The plug 37 may be removed when desired to permit the needle hub 36 to be connected into a hemodialysis blood circuit.

The described type of venipuncture device 10 is conventional and is used primarily for single needle hemodialysis. Clearly, any device in which the penetrating stylet needle is not rigidly secured to the catheter may be used with the instant invention. Attention is now turned to the structure and operation of the needle restraining collar 12 whereby longitudinal movement of the stylet needle 32 relative to the catheter 14 is prevented during the venipuncture process.

The needle restraining collar 12 shown in FIGS. 1-3 is constructed of heat-shrinkable plastic. Thus, when heated, the needle restraining collar 12 conforms to the surface contour of the venipuncture device 10 as illustrated in FIGS. 1-3. It should be particularly noted that when shrunk, the leading end of the needle restraining collar 12 forms as annular shoulder 42 which fits tightly around the forwardly projecting flange 26 of the hub 25 of the tube adaptor 16. In similar fashion, the rear end of the needle restraining collar 12 forms an annular shoulder 44 which fits tightly over the radially projecting flange 38 of the needle hub 36. The tight nonslip fit of the leading and trailing ends of collar 12 over flanges 26 and 38 prevents the stylet needle 32 from slipping during insertion, as will be hereinafter explained.

As shown best in FIG. 2, a longitudinal tear strip 46 is provided on the needle restraining collar 12 which may be used to release the collar 12. The longitudinal tear strip 46 is defined by two lines 48 and 50 scribed lengthwise along the needle restraining collar 12 as shown in FIG. 1. The lines 48 and 50 scribed on the needle restraining collar 12 allow the longitudinal tear strip 46 to be separated from the needle restraining collar 12 in the manner shown in FIG. 2. The tear strip 46 also has a tab 52 which extends to the rear of the needle restraining collar 12 so as to be finger accessible. Thus, in order to release the needle restraining collar 12 so as to permit its removal from the venipuncture device 10, it is only necessary to pull the tab 52 forwardly as shown in FIG. 2. Thereafter, the longitudinal tear strip 46 will separate along the lines 48 and 50 leaving an open slot 54 in the needle restraining collar 12 which permits removal of the collar from the venipuncture device 10.

As described previously, when the venipuncture device 10 is used to make a venipuncture in a patient's arm a rearwardly directed force is applied to the stylet needle 32 at the beveled point 34. Ordinarily, this rearwardly directed force would cause the stylet needle 32 to slip over to the rear through the catheter 14 until the beveled point 34 is obscured by the catheter 14. However, the annular shoulder 44 surrounding the radially projecting flange 38 of the needle hub 36 prevents the needle 32 from slipping to the rear. Furthermore, the annular shoulder 42 which surrounds the forwardly projecting flange 26 of the hub 25 of the tube adaptor 16 prevents the needle restraining collar 12 from slipping to the rear over the hub 25. Thus, it will be seen that the needle restraining collar 12 serves to prevent longitudinal movement of the stylet needle 32 relative to the catheter 14 of the venipuncture device 10 during insertion into a patient's arm. After the venipuncture has been made, the needle restraining collar 12 may be released by pulling the tab 52 forward as previously described thereby permitting removal of the needle restraining collar 12 from the venipuncture device 10 as shown in FIG. 3. The stylet needle 32 may then be withdrawn rearwardly through catheter 14, tube adaptor 16, sleeve 28 and rubber membrane 30 leaving only the catheter 14 in the patient's arm.

Having now described the embodiments illustrated in FIGS. 1-3, attention is turned to the needle restraining apparatus shown in the embodiments of FIGS. 4-10.

The Embodiments of FIGS. 4-10

Figure 4:
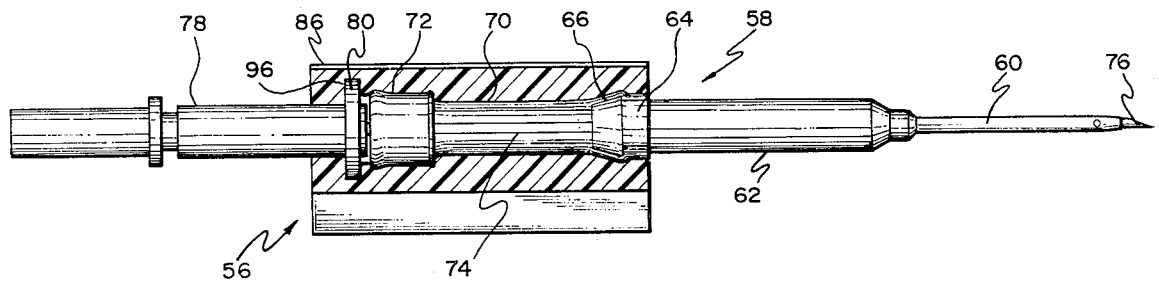
FIG. 4 is a side elevational view shown partially in cross section of another presently preferred embodiment of the needle restraining apparatus used in conjunction with a venipuncture device having a single channel tube adaptor.

FIG. 4 is a side elevational view shown partially in cross section of another preferred embodiment of the present invention. The needle restraining collar generally designated 56 in FIG. 4 may be used, for example, with a venipuncture device generally designated 58. The venipuncture device 58 has a radiopaque teflon catheter 60 which is attached to a tube adaptor 62. The venipuncture device 58 shown in FIG. 4 differs from the venipuncture device 10 shown in FIG. 1 only in that the FIG. 4 configuration has a single passageway, rather than the Y-configuration.

The tube adaptor 62 has a hub 64 which has a forwardly projecting frustoconically shaped flange 66. Flange 66 is used to help secure the needle restraining collar 56 to the hub 64 of tube adaptor 62 as hereinafter described. The hub 64 of the tube adaptor 62 fits in telescopic relation within a silastic sleeve 70 in the same manner as that described in connection with FIGS. 1-3. A rubber membrane 72 is provided at the rear end of the sleeve 70 which seals the channel formed by the sleeve 70 and tube adaptor 62 when the stylet needle 74 is withdrawn from the venipuncture device 58.

The hollow metallic stylet needle 74 projects telescopically forward through the membrane 72, sleeve 70, tube adaptor 62 and teflon catheter 60 so that the sharpened beveled point 76 extends beyond the tapered distal end of the catheter 60. The stylet needle 74 is attached at its rear end to a needle hub 78. The needle hub 78 has a radially projecting flange 80 at its forward end which is used to help secure the needle restraining collar 56 to the needle hub 78.

Figure 5:
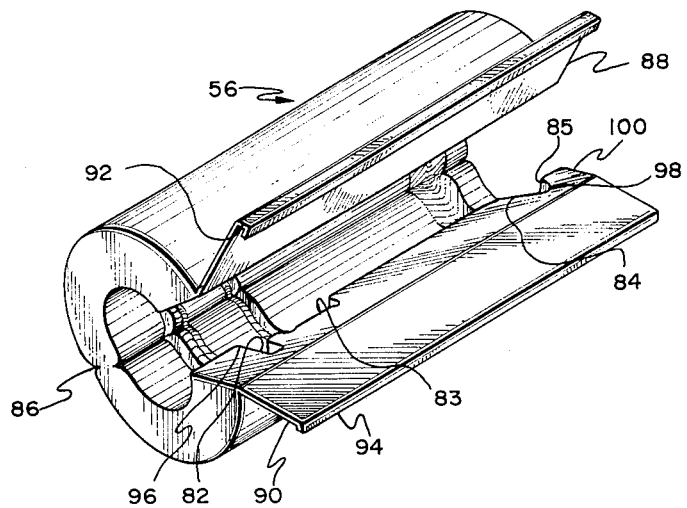
FIG. 5 is an enlarged perspective illustration of the collar of FIG. 4 particularly illustrating the structure for accommodating release of the collar.

The needle restraining collar 56 shown in FIGS. 4 and 5 is constructed of molded plastic. As more clearly shown in FIG. 5, concentric grooves 82-84 are formed in the inside surface of the needle restraining collar 56. The concentric grooves 82-84 are designed to fit snugly around the radially projecting flange 80 of the needle hub 78, the membrane 72, and the forwardly projecting flange 66 of the hub 64 of the tube adaptor 62.

As further illustrated in FIG. 5, the needle restraining collar 56 has a cross-sectionally reduced portion along its length which forms a hinge 86. It should be noted that when the needle restraining collar 56 is constructed of molded plastic having memory, the hinge 86 may be biased towards an open position. Thus, when opened, the hinge 86 will return the collar 56 to the open position. Alternatively, the hinge 86 could be designed so that the needle restraining collar 56 would be frangible along the length of hinge 86 thereby allowing the collar 56 to separate into two halves when opened which would then fall off of the venipuncture device 58.

The needle restraining collar 56 shown in FIGS. 4 and 5 also has a top tab 88 and a bottom tab 90 which are used in opening and closing the collar 56. The top tab 88 has an L-shaped groove 92 formed in the distal end of the tab 88 which acts as a latch. The bottom tab 90 has a downwardly bent lip 94 adapted to fit within the groove 92 of the top tab 88. In order to separate the tabs 88 and 90 when closed, it is only necessary to bend tab 88 upwards until the bottom tab 90 is separated therefrom.

During the venipuncture process, the needle restraining collar 56 acts to restrain longitudinal movement of the stylet needle 74 relative to the catheter 60 is the following manner. As a rearwardly directed force is applied to the stylet needle 74 at the beveled point 76 during insertion, the radially projecting flange 80 of the needle hub 78 is forced against the shoulder 96 formed along the trailing side of the concentric groove 82 which surrounds the radially projecting flange 80. The shoulder 96 abuts the radially projecting flange 80 and prevents the needle hub 78 from moving to the rear. At the same time, the annular shoulder 98 formed along the leading end of the concentric groove 84 abuts the irregular contour of the sleeve 70 surrounding the flange 66 of hub 64 of the tube adaptor 62 thereby preventing the collar 56 from being pulled off of the hub 64. In this manner, it will be seen that the needle restraining collar 56 prevents longitudinal movement of the stylet needle 74 relative to the catheter 60 during venipuncture, thereby insuring that the beveled point 76 remains exposed so that it makes the puncture in the patient's skin.

Figure 6:
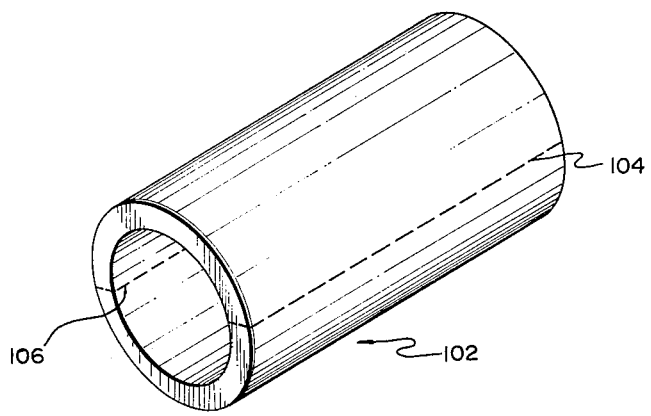
FIGS. 6, 7 and 8 are perspective illustrations of other embodiments of needle restraining apparatus showing different structures accommodating release of the collar.

The needle restraining collar generally designated 102 shown in FIG. 6 differs from that shown in FIG. 5 primarily in the manner in which the needle restraining collar 102 is released. Lines 104 and 106 are scribed lengthwise along the needle restraining collar 102 on the inside and outside surfaces of the needle restraining collar 102. The lines 104 and 106 scribed on the needle restraining collar 102 cause the collar 102 to be frangible along the lines 104 and 106. Thus, when the needle restraining collar 102 is pinched in or compressed, it will crack along the lines 104 and 106 thereby forming two halves of the needle restraining collar 102 which may be removed from the venipuncture device (not shown). Alternatively, a thumbnail may be run along the line 104 or 106.

Figure 7:
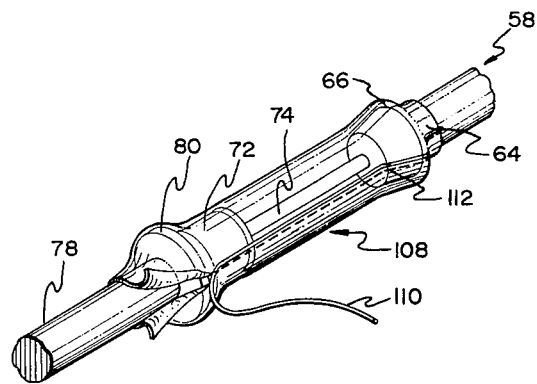

The needle restraining collar generally designated 108 shown in FIG. 7 is made of heat-shrinkable plastic in the same manner as the embodiment described above in connection with FIGS. 1-3. The needle restraining collar 108 of FIG. 7 differs from the needle restraining collar 12 of FIGS. 1-3 primarily in the manner in which the needle restraining collar 108 is released.

As will be seen from FIG. 7, a single line 112 is scribed along the entire length of needle restraining collar 108. The line 112 causes the collar 108 to be frangible along the line as hereinafter more fully described. Needle restraining collar 108 is also provided with a lanyard 110 located along the inside of the collar 108 adjacent the scribed line 112. It will be noted that the lanyard 110 is long enough so that the trailing end of the lanyard 110 extends beyond the trailing end of the needle restraining collar 108. This allows the trailing end of lanyard 110 to be finger accessible.

In order to release the needle restraining collar 108 shown in FIG. 7, it is only necessary to pull the end of the lanyard 110 forward. As the lanyard 110 is pulled forward, it will cause the collar 108 to separate along the frangible line 112 scribed along the length of the collar 108 in the manner illustrated in FIG. 7. In this manner, the needle restraining collar 108 can be fully released and thereby removed from the venipuncture device 58.

Figure 8:
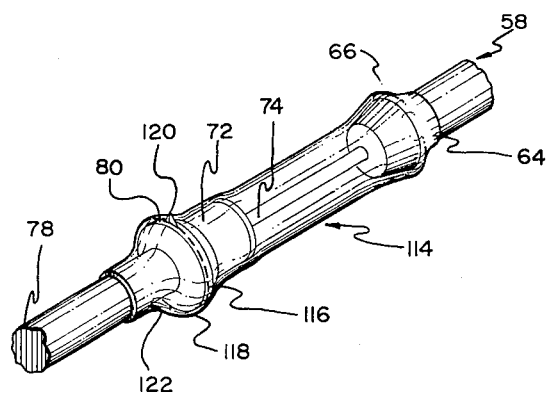

The needle restraining collar generally designated 114 illustrated in FIG. 8 is also made of heat-shrinkable plastic such as the embodiments described in connection with FIGS. 1-3 and FIG. 7. As illustrated in FIG. 8, the collar 114 has a line 116 scribed circumferentially around an annular shoulder 118 of the collar 114 which is shrunk to fit tightly over the radially projecting flange 80 of the needle hub 78. The radially projecting flange 80 of needle hub 78 is provided with a sharp protruding point 120 which projects through the line 116 scribed around the circumference of annular shoulder 118.

In order to release the needle restraining collar 114 the collar 114 is rotated relative to the needle hub 78 so that the sharp protruding point 120 slices the needle restraining collar 114 along the line 116 around the circumference of the annular shoulder 118. This allows the trailing end 122 of the needle restraining collar 114 to be completely separated from the needle restraining collar 114 thereby permitting withdrawal of the stylet needle 74 from the venipuncture device 58.

Figure 9:
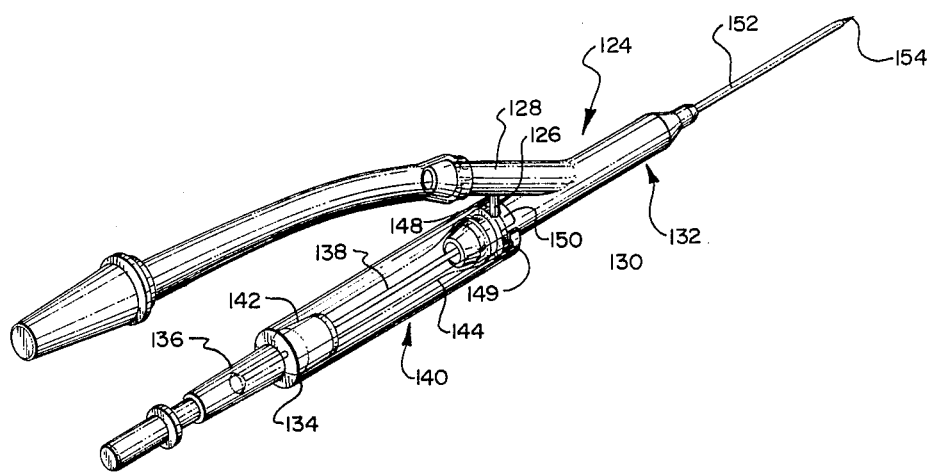
FIG. 9 is a perspective illustration of another presently preferred embodiment of the needle restraining apparatus used with a venipuncture device having a Y-channel tube adaptor.
Figure 10:
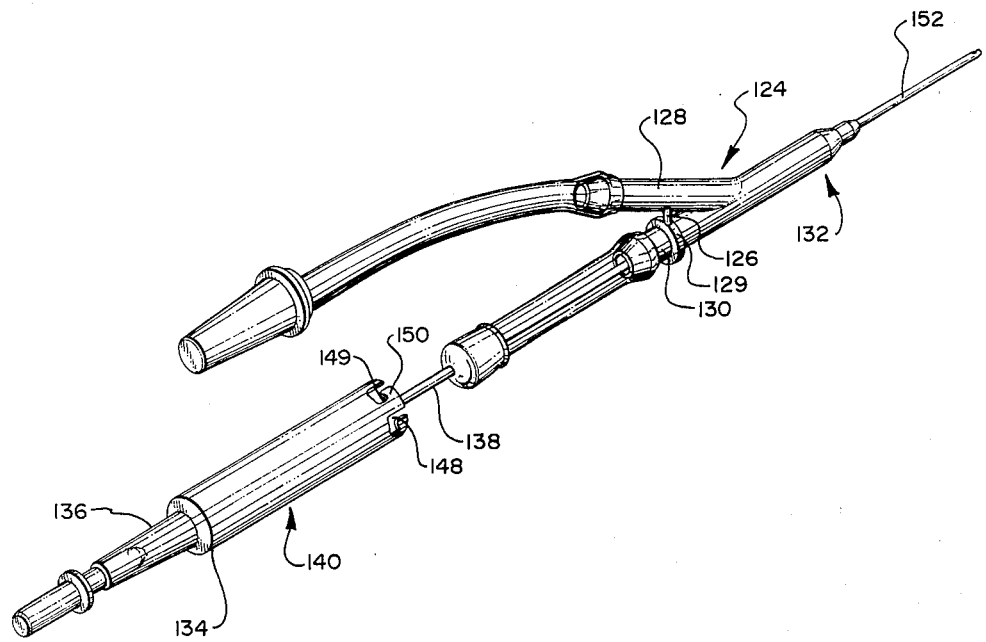
FIG. 10 is a perspective illustration of the apparatus of FIG. 9, showing the needle partly withdrawn from the catheter and tube adaptor after the collar has been released.

FIGS. 9 and 10 illustrate another presently preferred embodiment of the needle restraining collar in combination with a venipuncture device which has been slightly modified to accommodate the needle restraining collar. The tube adaptor 132 of venipuncture device 124 of FIGS. 9 and 10 differs from the venipuncture device 10 of FIGS. 1–3 in the addition of a small dowel-shaped keeper 126 located near the juncture formed between the body portion 130 and the branch 128 of tube adaptor 132. A similar keeper could be provided opposite keeper 126 to enhance the needle restraining action, as described below, if so desired.

As shown more clearly in FIG. 10, the needle restraining collar generally designated 140 is a cylindrically shaped plastic shell. The trailing end of collar 140 is rigidly affixed to the radially projecting flange 134 of needle hub 136.

The inside diameter of collar 140 is sufficiently large to allow the collar 140 to slide over the membrane 142 and sleeve 144 as illustrated in FIG. 9. The overall length of the collar 140 is slightly shorter than the combined length of membrane 142 and sleeve 144 for purposes to be hereinafter more fully described.

The leading end of collar 140 contains four generally L-shaped slots such as the two shown at 148 and 149. The four L-shaped slots are spaced 90° apart around the circumference of the leading end. A small detent such as that illustrated at 150 is formed at the base of each slot. Each of the four slots is positioned so as to permit the bevel of the point 154 of stylet needle 138 to be positioned either up or down or facing laterally to either side. This allows the user of the venipuncture device 124 a greater choice as to the manner in which the device 124 is held while making a venipuncture. Thus, for example, when the stylet needle 138 is locked by using slot 148, the bevel of the point 154 will face upward thereby allowing the user of the venipuncture device 124 to insert the device 124 into the patient's arm with the channel 128 in an upward position. In like manner, the position of the beveled point 154 may be locked using other slots so as to allow the venipuncture device 124 to be inserted with the channel 128 in a downward position or flat to either side.

In order to restrain longitudinal movement of the stylet needle 138 during venipuncture, a slot such as that at 148 is aligned with the dowel-shaped keeper 126. The collar 140 is then pressed onto the keeper 126 and rotated so that the detent 150 engages the keeper 126. It should be noted that since the length of the collar 140 is slightly less than the overall length of membrane 142 and sleeve 144, the rubber membrane 142 and silastic sleeve 144 will be slightly compressed, thereby exerting a small force against the collar 140 which will insure that the collar 140 stays locked into position since the detent 150 will be urged against the keeper 126. Thus, as a rearwardly directed force is applied to the point 154 of stylet needle 138 during venipuncture, lateral motion to the rear will be prevented since the collar 140 will be locked at the leading end to the tube adaptor by reason of the coaction of keeper 126 and detent 150 and since the collar 140 is also rigidly affixed to the radially projecting flange 134 of needle hub 136. Thus, it will be seen that the needle restraining collar 140 effectively prevents the stylet needle 138 from slipping to the rear during venipuncture.

In order to release the needle restraining collar 140, collar 140 is first forced forward against the bias of the membrane 142 and sleeve 144, thereby releasing it from keeper 126. The collar 140 is then rotated so that the slot 148 and keeper 126 are again aligned. The stylet needle 138 together with the collar 140 which is rigidly affixed to the radial flange 134 of needle hub 136 may then be withdrawn as illustrated in FIG. 10. When completely withdrawn, the self-sealing membrane 142 will prevent leakage of blood or other fluids as described above.

The invention may be embodied in other specific forms without departing from its spirit or essential characteristics. The described embodiments are to be considered in all respects only as illustrative and not restrictive and the scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. In an improved venipuncture device comprising a needle portion including a hub means on one end and a sharpened tip at the other end and a catheter portion, said needle portion extending coaxially through the catheter portion so as to expose the distal end of the needle portion, said venipuncture device further comprising a flexible sleeve joined to the catheter portion and surrounding a part of the needle portion, the improvement comprising:

a needle restraining means which fits over substantially the entire length of the flexible sleeve, said restraining means being joined at one end to the catheter portion and joined at the other end to the needle portion at the hub means, said means preventing coaxial movement of the needle portion with respect to the catheter portion during venipuncture, said restraining means further comprising means for removing the restraining means off from the flexible sleeve so as to permit the needle portion to be completely withdrawn after venipuncture.

2. In a venipuncture device comprising a needle portion with a hub means on one end and a sharpened tip at the other end thereof, a catheter portion which fits telescopically over the needle portion, and a flexible sleeve joined to the catheter portion and surrounding a part of the needle portion, a needle restraining collar for preventing said needle portion from longitudinally moving relative to the catheter portion of the device during insertion, said collar fitting over substantially the entire length of the flexible sleeve and comprising:

first restraining means for releasably securing the leading end of the collar around at least a part of the catheter portion of the device;

second restraining means for releasably securing the trailing end of the collar around the hub means of the needle portion of the device, thereby preventing longitudinal movement of the needle portion relative to the catheter portion; and means for removing the collar so as to allow the needle portion to be completely withdrawn from the catheter portion.

3. Needle restraining apparatus as defined in claim 2 wherein said first restraining means comprise a plurality of concentric grooves formed in the leading end of the collar, said grooves engaging a part of the contour of the catheter portion so as to prevent the collar from slipping rearwardly off the catheter portion.

4. Needle restraining apparatus as defined in claim 2 wherein said second restraining means comprise a concentric groove formed in the trailing end of the collar, said groove engaging a part of the contour of the needle portion so as to prevent the collar from slipping forwardly off the needle portion.

5. Needle restraining apparatus as defined in claim 2 wherein said releasing means comprise a latch located on the collar which when unhooked releases the collar.

6. Needle restraining apparatus as defined in claim 5 wherein said releasing means further comprise a frangible hinge which is formed along the length of the collar and which allows the collar to separate at the hinge when the collar is unlatched.

7. Needle restraining apparatus as defined in claim 5 wherein the collar is constructed of rigid molded plastic having memory, the memory of said plastic collar being biased towards the open position so that when the latch on the collar is released it will return to the open position.

8. Needle restraining apparatus as defined in claim 2 wherein said releasing means comprise at least one line scribed longitudinally along the length of the surface of the collar, said line causing the collar to be frangible along the line so that the collar can be opened along said line.

9. In a venipuncture device having a needle portion with a hub and a catheter portion with a tube adaptor fitting telescopically over said needle portion, a needle restraining collar for preventing said needle portion from moving longitudinally with respect to the catheter portion during venipuncture, the collar comprising;

a leading end having a shoulder formed therein, the shoulder engaging a part of the contour of the tube adaptor of the catheter portion so as to prevent the collar from rearwardly slipping off the tube adaptor;

a trailing end having a shoulder formed therein, the shoulder engaging a part of the contour of the hub of the needle portion so as to prevent the collar from slipping forwardly off the hub of the needle portion;

a narrow membrane formed longitudinally along the length of the collar, said membrane acting as a hinge for the collar; and a latch which may be selectively released to allow the collar to open so that the needle portion can be withdrawn from the rear end of the catheter portion.

10. In a venipuncture device comprising a needle portion having a hub means on one end and a sharpened tip at the other end thereof, a catheter portion having a hub means at one end thereof, said catheter portion fitting telescopically over said needle portion, and a flexible sleeve joined to the catheter portion and surrounding a part of the needle portion, a needle restraining collar for preventing said needle portion from longitudinally moving relative to the catheter portion, said collar spanning substantially the entire length of the flexible sleeve and comprising:

means for releasably conforming in nonslip relation to (1) the hub means of the catheter portion of the device and (2) the hub means of the needle portion of the device, thereby preventing the needle portion from longitudinally moving relative to the catheter portion; and means for removing the collar so as to allow the needle portion to be completely withdrawn from the catheter portion.

11. Needle restraining apparatus as defined in claim 10 wherein said releasing means comprise a longitudinal strip on the collar which when pulled opens the collar sufficiently to permit its removal from the venipuncture device.

12. Needle restraining apparatus as defined in claim 10 having at least one line scribed longitudinally along the length of the surface of the collar, said line causing the collar to be frangible along the line so that the collar can be opened along said line.

13. Needle restraining apparatus as defined in claim 12 having a lanyard located along the inside surface of the collar adjacent the longitudinally scribed line, said lanyard having an end which is finger accessible and which when pulled causes the lanyard to open the collar along the line.

14. Needle restraining apparatus as defined in claim 10 wherein said venipuncture device comprises a sharp point located on the needle portion and wherein said releasing means comprise a line scribed circumferentially on the surface of the collar, said line being located so as to coact with the sharp point on the needle portion by severing the collar along the line with the sharp point as the collar is rotated with respect to the needle portion.

15. In a venipuncture device having a needle portion and a catheter portion which fits telescopically over the needle portion, a restraining collar for preventing said needle portion from longitudinally moving relative to the catheter portion during venipuncture, the collar comprising:

a leading end which when heated shrinks over the contour of at least part of the catheter portion, thereby preventing the collar from rearwardly slipping off the catheter portion;

a trailing end which when heated shrinks over the contour of at least part of the needle portion, thereby preventing the collar from slipping forwardly off the needle portion; and a plurality of lines scribed longitudinally along the surface of the collar, said lines defining a strip of the collar which may be selectively opened, whereby permitting the collar be removed so that the needle portion can be withdrawn through the rear end of the catheter portion.

16. Needle restraining apparatus as defined in claim 15 wherein said strip which may be selectively opened further comprises a rearwardly projecting tab attached at the trailing end of the strip, said tap being finger accessible so as to facilitate use of the strip to open the collar.

17. A method of restraining coaxial movement of a needle portion of a venipuncture device relative to a catheter portion of said device, said device comprising a needle portion including a hub means on one end and a sharpened tip at the other end thereof, a catheter portion through which said needle portion extends coaxially, and a flexible sleeve circumscribing part of the length of the needle portion, the method comprising the steps of:
- providing a needle restraining collar which fits over substantially the entire length of the flexible sleeve;
- interposing said needle restraining collar between the needle portion and the catheter portion;
- releasably joining one end of the restraining collar to the catheter portion and joining the other end to the hub means of the needle portion so as to prevent coaxial movement of the needle portion relative to the catheter portion; and
- removing the collar after venipuncture to thereby permit the needle portion to be completely withdrawn.

18. A venipuncture device comprising in combination:
- a catheter;
- a hollow tube adaptor joined at its forward end to one end of said catheter, the hollow of said adaptor communicating with the lumen of said catheter;
- a hollow flexible sleeve elastically stretched over a portion of the rear end of said tube adaptor;
- a dowel-shaped keeper attached to the rear end of said adaptor; and
- a hollow stylet needle extending coaxially through the hollow of said sleeve, the hollow of said tube adaptor, and the lumen of said catheter, thereby exposing the tip of said stylet needle beyond the distal end of the catheter, said needle having a hub comprising a cylindrical collar which fits over said elastic sleeve, said collar having a slot formed in the leading end thereof which coacts with the keeper to lock the needle relative to the catheter.

19. A venipuncture device as defined in claim 18 further comprising a plurality of slots formed in the leading end of said collar, each said slot corresponding to a predetermined position for the tip of the stylet needle.

20. A venipuncture device as defined in claim 18 wherein the length of said collar is slightly less than the length of said flexible sleeve, thereby causing the sleeve to be compressed when the slot of the collar engages the keeper, said compression exerting sufficient force on the collar to lock said keeper in the slot.

* * * * *